Figure 1:
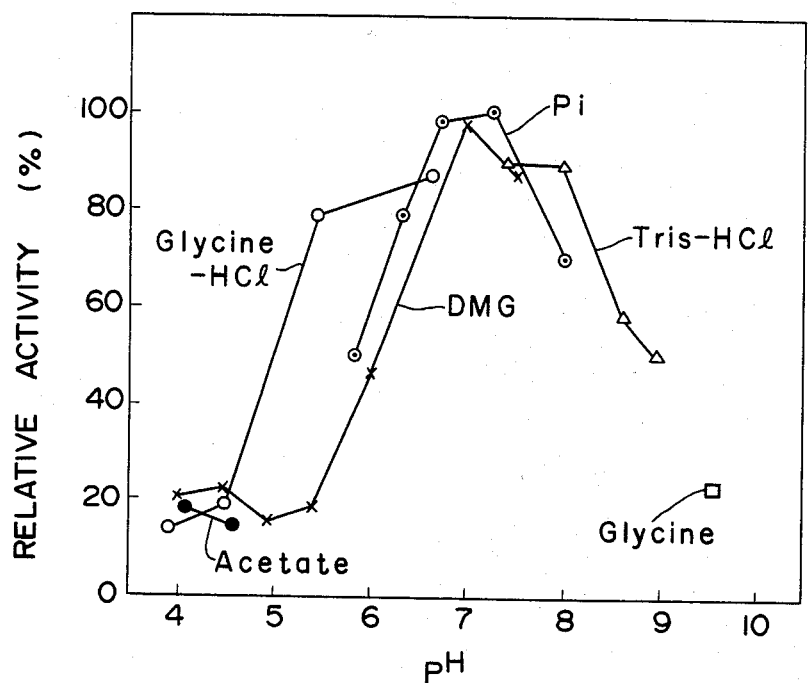

United States Patent [19]

Yoshino et al.

[11] Patent Number: 4,496,655

[45] Date of Patent: Jan. 29, 1985

[54] PROCESS FOR THE PRODUCTION OF TYRAMINE OXIDASE

[75] Inventors: Eiichi Yoshino; Kazuo Matsuura; Hideo Misaki, all of Shizuoka, Japan

[73] Assignee: Toyo Jozo Kabushiki Kaisha, Shizuoka, Japan

[21] Appl. No.: 454,060

[22] Filed: Dec. 28, 1982

[30] Foreign Application Priority Data

Dec. 28, 1981 [JP] Japan .................................. 56-209676

[51] Int. Cl.³ ............................ C12N 9/06; C12Q 1/36; C12Q 1/26; C12R 1/06
[52] U.S. Cl. .................................... 435/191; 435/830; 435/24; 435/25
[58] Field of Search ............................... 435/191, 189

[56] References Cited

PUBLICATIONS

Archives of Microbiology vol. 129, pp. 72–80, (1981).
Methods in Enzymology vol. 17B pp. 722–726, (1971).
Enzyme Nomenclature 1978, pp. 82–83.

*Primary Examiner*—Lionel M. Shapiro
*Attorney, Agent, or Firm*—Young & Thompson

[57] ABSTRACT

Tyramine oxidase, which is useful for the clinical diagnosis of leucine aminopeptidase activity in serum, is produced by culturing the microorganism Arthrobacter sp. B-0813 FERM-P No. 6240 in a nutrient medium, and isolating thus-produced tyramine oxidase from the cultured medium.

3 Claims, 4 Drawing Figures

PROCESS FOR THE PRODUCTION OF TYRAMINE OXIDASE

This invention relates to a process for the production of tyramine oxidase by fermentation. More particularly, the present invention pertains to a process for the production of tyramine oxidase, which comprises culturing a tyramine-oxidase-producing microorganism belonging to the genus Arthrobacter in a nutrient medium, and isolating thus-produced tyramine oxidase from the cultured medium.

Tyramine oxidase has specific action on tyramine (p-hydroxyphenylethylamine), and catalyzes a reaction which produces one mole of p-hydroxybenzylaldehyde, one mole of hydrogen peroxide and one mole of ammonia from one mole of tyramine, one mole of oxygen and one mole of water. The said enzyme does not act on L-leucyltyramine, and hence is preferable for clinical diagnosis of leucine aminopeptidase (LAP) activity in serum. Namely, synthetic substrate L-elucyltyramine is treated with LAP to liberate tyramine, which is oxidized by tyramine oxidase, then the consumed oxygen or generated hydrogen peroxide or ammonia is measured by means of conventional electric means, colorimetric means or fluorometric means to assay LAP. Tyramine oxidase does not act on the synthetic substrate and acts on tyramine alone, and hence LAP activity can be exactly measured.

Production processes for tyramine oxidase have been reported in *J. Bacteriol.*, 127 (1), 24–31 (1976), *Igaku to Seibutsugaku* (Medical and Biological Sciences, in Japanese), 91 (4), 233–236 (1975), *J. Bacteriol.*, 145 (2), 796–802 (1981) and *Agr. Biol. Chem.*, 31 (8), 897–901 (1967).

We have found that a microorganism strain B-0813 belonging to the genus Arthrobacter isolated from a soil sample collected at Kanogawa Sewage Plant, Toyo Jozo K.K., Ohito-cho, Tagata-gun, Shizuoka-ken, Japan, produces tyramine oxidase when cultured in a nutrient medium.

The taxonomical properties of Arthrobacter sp. B-0813 FERM-P No. 6240 are as follows:

I. Morphological properties:
 Observations on bouillon agar plate cultured at 30° C. for 6–24 hours are as follows:
 Juvenile cells grown during six hours cultivation are straight or slightly curved rods or short rods with round edges, single, double or short chains and $0.4\times0.5$–$1.2$ μm in size.
 Old cells cultured more than 24 hours are globose or short rods with round edges, single, double or short chains and $0.4\times0.4$–$0.5$ μm in size. The cells are: polar flagella or subpolar flagella with motility, no formation of spores, Gram positive, sometimes Gram negative according to culturing time, and negative acid-fast stain.

II. Growth on various media:
 Observations on various media cultured at 30° C. for 1–7 days are as follows:
 Bouillon agar plate: circular, smooth periphery, planar, humectous colony, grayish white to pale yellow after a few days culture.
 Bouillon agar slant: good growth, filiform growth, grayish white to pale yellow, no production of soluble pigment.
 BCP milk medium: cultured for 14 days with added bromcresol blue; weakly alkaline, no coagulant peptonization.

III. Physiological properties:
 Nitrate reduction: +
 Denitrate reaction: −
 MR-test: −
 VP-test: −
 Indole formation: −
 $H_2S$ formation: −
 Starch hydrolysis: +
 Citrate utilization:
  Simons medium: +
  Chrystenssen medium: +
 Nitrate utilization: +
 Ammonium utilization: +
 Soluble pigment formation: −
 Urease:
  SSR medium: −
  Chrystenssen medium: −
 Oxidase: −
 Catalase: +
 Growth pH: 5.5–9.5
 Growth temperature: 10°–42° C.
 Nature: aerobic
 OF-test (Hugh-Leifson medium): NT (alkaline)
 OF-test (modified medium): O
  Modified medium: $NH_4H_2PO_4$ 1 g, KCl 0.2 g, $MgSO_4.7H_2O$ 0.2 g, yeast extract 1 g, agar 3 g, BTB (bromthymol blue, 10%) 10 ml, distilled water 1000 ml, pH 7.0.
 Acid formation from sugar (basal medium and modified medium are used; no gas formation was observed):
  Acid formation: cellobiose, D-fructose, D-glucose, glycerol, maltose, D-mannose, melezitose, trehalose.
  No acid formation: adonitol, L-arabinose, dulcitol, mesoerythritol, fucose, D-galactose, inositol, inulin, lactose, D-mannitol, raffinose, L-rhamnose, salicin, L-sorbose, sorbitol, starch, saccharose, D-xylose.
 Esculin decomposition: −
 Cellulose decomposition: −
 Guanine and cytosine contents in DNA are 62.7% (Tm method).

According to the above taxonomic properties, the strain B-0813 is: positive Gram's stain, mobile by polar flagella or subpolar flagella, juvenile cells (approximately 6 hours culture) rod or short rod shaped with round edges, straight or curved, $0.4\times0.5$–$1.2$ μm in size, old cells (more than 24 hours culture) short rods or globose, $0.4\times0.4$–$0.5$ μm in size, oxidative decomposition of sugar in a medium containing peptone, positive catalase, negative oxidase and not auxotrophic. As a result, consulting *Bergey's Manual of Determinative Bacteriology*, 8th Ed. (1974), the strain B-0813 belongs to the genus Arthrobacter of Coryneform group bacteria. Therefore, the strain B-0813 is referred to as Arthrobacter sp. B-0813 and has been deposited in the Fermentation Institute, Agency of Industrial Technology and Science, MITI, Japan as permanent culture collection FERM-P No. 6240.

The strain which can be used in the present invention is, for example, Arthrobacter sp. B-0813 FERM-P No. 6240. The invention is not limited to this strain, however, as other tyramine-oxidase-producing strains can be used, belonging to the above genus.

Figure 2:
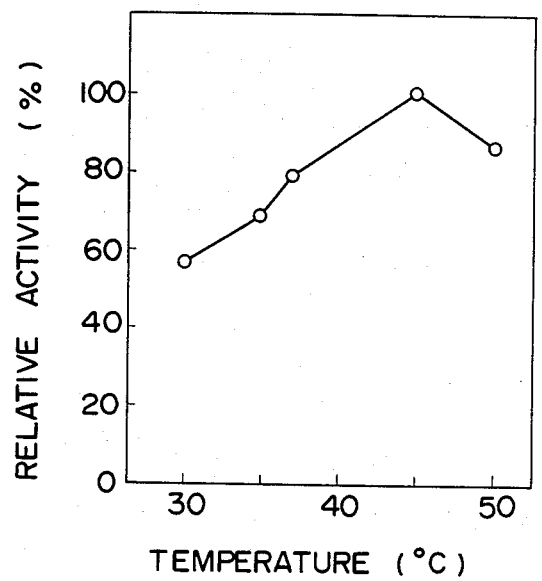
Figure 3:
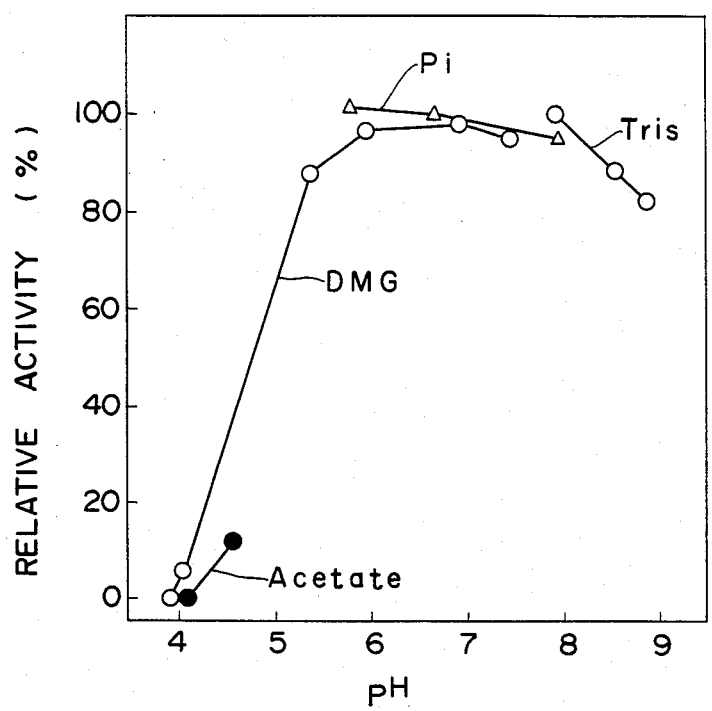
Figure 4:
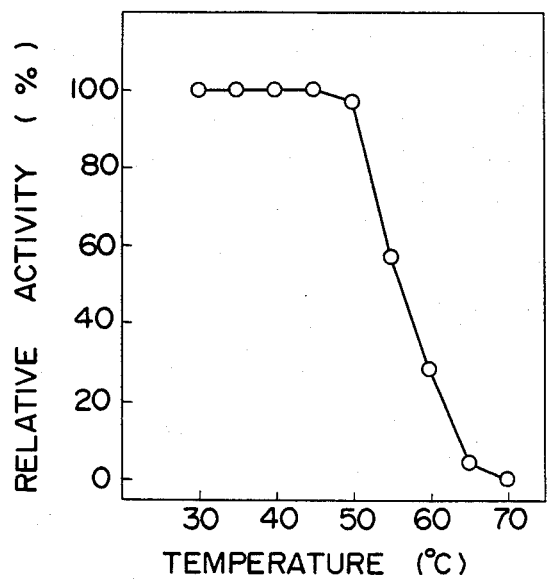

In the accompanying drawings:
FIG. 1 is a graph of optimum pH of the engine of various buffers;

FIG. 2 is a graph of optimum temperature;
FIG. 3 is a graph of stability at various pH's in various buffers; and
FIG. 4 is a graph of stability at various temperatures.

In a preferred embodiment of the present invention, a nutient medium comprising soybean oil 0.8%, corn steep liquor 1.0%, meat extract 1.0%, polypeptone 0.5%, NaCl 0.3% and β-phenylethylamine 0.15% (pH 7.5) is used, and the strain is aerobically submerged cultured at 30° C. for 20 hours. Tyramine oxidase is accumulated in the cultured cells.

The biochemical properties of the enzyme are as folows:

(1) Enzymatic action:
Action on tyramine and not L-leucyltyramine.
The enzyme catalyzes a reaction which forms one mole of p-hydroxybenzylaldehyde, one mole of hydrogen peroxide and one mole of ammonia from one mole of tyramine, one mole of oxygen and one mole of water.

(2) Assay method of enzyme:
An enzyme solution (0.05 ml) is added to a reaction mixture (0.5 ml) consisting of the following, and the volume is increased to 1.0 ml by adding water and the mixture is incubated at 37° C. for 10 minutes. 1% cetylpyridinium chloride (2.0 ml, pH 7.0) is added to stop the reaction.

| | |
|---|---|
| 0.2 M phosphate buffer (pH 7.5) | 0.1 ml |
| 0.2% phenol | 0.1 ml |
| 0.3% 4-aminoantipyrine | 0.1 ml |
| (500 U/ml) peroxidase (horseradish) | 0.1 ml |
| 1 mM tyramine | 0.1 ml (0.1 mM) |

Water (0.1 ml) is added in place of enzyme solution as a control. The reaction mixture is measured at 490 nm.

Enzyme activity is calculated by the following equation:

$$U/ml = \frac{\Delta 490nm}{12 \times \frac{1}{2}} \times \frac{3}{0.05 \text{ (ml)}} \times \frac{1}{10 \text{ (min.)}} \times f$$

wherein Δ490 nm is the absorption value at Δ490 nm for 10 minutes, and f is the dilution ratio.

(3) Molecular weight:
48,000 [Gel-filtration method using Sepharose CL-6B (trademark)]

(4) Isoelectric point:
pH 4.23 (electrophoresis using carrier ampholite)

(5) Km-value: $2.7 \times 10^{-5}$M (tyramine)

(6) Optimum pH:
Optimum pH is determined by assaying the enzyme activity in an acetate buffer, glycine-HCl buffer, dimethylglutarate-NaOH buffer, Tris-HCl buffer, phosphate buffer and glycine-NaOH buffer. The optimum pH of the enzyme is shown in FIG. 1, in which the optimum pH value is at approximately pH 7.0.

(7) Optimum temperature:
The pH of the reaction mixture is adjusted to pH 7.5 and the mixture is assayed at various temperatures. The results are shown in FIG. 2, in which the optimum temperature is at approximately 45° C.

(8) pH-stability:
The enzyme solution is added to buffers of various pH, namely, to acetate buffer, dimethylglutaryl-NaOH buffer, phosphate buffer and Tris-HCl buffer, the mixtures are incubated at 37° C. for 60 minutes, and the remaining activity is assayed. The results are shown in FIG. 3 in which the enzyme is stable at pH 6–8.

(9) Heat stability:
The enzyme is heated at pH 7.5 at 30°–70° C. for 5 mins. in the reaction mixture used in the assay method, and the remaining enzyme activity is assayed. The results are shown in FIG. 4, in which the enzyme is stable up to 45° C.

(10) Effect of various substances:
The effect of various substances on the activity of tyramine oxidase is shown in the following table:

| Substance | Amount Added (mM) | Relative Activity (%) |
|---|---|---|
| $NaN_3$ | 5 | 98.3 |
| $NaMoO_4$ | 5 | 39.7 |
| KCN | 5 | 100.0 |
| $NH_4Cl$ | 5 | 96.6 |
| LiCl | 5 | 82.8 |
| $CoCl_2$ | 5 | 86.2 |
| $MnCl_2$ | 5 | 82.8 |
| $CaCl_2$ | 5 | 86.2 |
| $BaCl_2$ | 5 | 96.6 |
| p-chloromercuribenzoate (PCMB) | 0.2 | 79.3 |
| EDTA | 5 | 100.0 |
| FMN | 0.01 | 108.8 |
| FAD | 0.1 | 75.4 |
| Cetylpyridinium chloride | 0.025 | 0.0 |
| Cetyltrimethylammonium chloride | 0.025 | 0.0 |
| Cation FB (trademark) | | 21.3 |
| Laurylbenzene sulfonate (LBS) | 0.05 | 63.9 |
| Bridge 35 (trademark) | 0.025 | 96.7 |
| Triton X-100 (trademark) | 0.025 | 96.7 |
| Control (no addition) | 0 | 100.0 |

As shown by the above, addition of flavin mononucleotide increases the activity of the enzyme.

(11) Substrate specificity:
Substrate specificity was measured by adding various substrates to the reaction mixture. The results are shown in the following table:

| Substrate | Relative activity (%) |
|---|---|
| Tyramine | 100.0 |
| β-phenylethylamine | 54.7 |
| p-chlorophenylethylamine | 47.9 |
| n-butylamine | 45.3 |
| Methylamine | 0.0 |
| Ethylamine | 0.0 |
| Benzylamine | 0.0 |
| Amino acids* | 0.0 |

*Amino acids: L-tryptophane, valine, phenylalanine, arginine, lysine, histidine, alanine, isoleucine, threonine, serine, aspartic acid, glutamic acid, methionine, tyrosine, D-glutamic acid, D-phenylalanine, D-alanine, DL-isoleucine, DL-valine, DL-tryptophane.

As shown by the above, the enzyme of the present invention shows specific activity on tyramine, and activity on β-phenylethylamine, p-chlorophenylethylamine or n-butylamine, and no activity on the other amines and amino acids.

The following examples illustrate the present invention.

EXAMPLE 1

A medium (100 ml, pH 7.5) comprising by weight soybean oil 0.8%, corn steep liquor 1.0%, meat extract 0.1%, polypeptone 1.0%, NaCl 0.3% and β-phenylethylamine 0.15% was put into a 500 ml Erlenmeyer flask and sterilized at 120° C. for 20 minutes. Arthrobacter sp. B-0813 FERM-P No. 6240 was inoculated into the medium and the mixture was cultured at 30° C. for 20 hours to prepare a seed culture. The medium containing the same components (20 lit.) together with added 0.2% of antifoam agent (silicone AF-145), (Asahi Chem.) was poured into a 30 lit. jar fermenter and the above two flasks of seed culture were inoculated therein, then the medium was aerobically cultured with agitation at 250 rpm and with 20 lit./min. aeration for 20 hours. The tyramine oxidase activity of the cultured broth was 1.3 U/ml.

When tyramine or butylamine was added to the medium, a more than 200-fold increase in the yield of enzyme was observed as compared with no addition of these amines. The amount of such addition is 0.1–0.2%, preferably 0.15%. The culturing temperature is generally 25°–35° C. and the culturing time is 10–30 hours.

EXAMPLE 2

Cultured broth (about 20 lit., 26,000 U) from Example 1 was centrifuged at 5000 rpm for 15 minutes. The separated material was washed with 20 mM phosphate buffer (pH 7.5) to obtain the bacterial cells. The cells were added to 20 mM phosphate buffer (pH 7.5, 4 lit.) containing EDTA (5 mM) and lysozyme (1 mg/ml) to lyse the cells. After bacteriolysis, the lysate was centrifuged at 5000 rpm for 15 minutes to obtain the supernatant solution. Saturated ammonium sulfate solution was added up to 40% V/V to the supernatant solution, and the precipitate was removed. Then the saturated ammonium sulfate solution was added to 90% V/V against the original supernatant solution. The thus-formed precipitate in the solution was poured onto a diatomaceous earth (Radiolite, trademark) layer, wherein the diatomaceous earth suspended in saturated ammonium sulfate was filtered through filter paper on a funnel to make about a 2 cm thick layer of diatomaceous earth, then the precipitate was collected by scratching the surface of the layer. The precipitate was dissolved in 20 mM phosphate buffer (pH 7.5, 500 ml), and the solution was centrifuged at 5000 rpm for 15 minutes. The supernatant solution was concentrated by an ultrafiltration membrane XM-50 (Amicon Co.) and desalted through a column of Sephadex G-25. The eluate was charged on a column ($7 \times 34$ cm) of DEAE-Sepharose CL-6B, and eluted by linear gradient elution with a 20 mM phosphate buffer (pH 7.5, 1 lit.) and 1.0M phosphate buffer (pH 7.5, 1 lit.) The fractions eluted over the concentration range of 0.5–0.7M were collected and concentrated by an ultrafiltration membrane XM-50. The concentrated solution was desalted by gel filtration through a column of Sepharose CL-6B with a 20 mM phosphate buffer (pH 7.5). The eluate was lyophilized to obtain a powder of tyramine oxidase (6.7 g, 0.5 U/mg).

What is claimed is:

1. A process for the production of tyramine oxidase, which comprises culturing Arthrobacter sp. B-0813 FERM-P No. 6240 in a nutrient medium, and isolating thus-produced tyramine oxidase from the cultured medium.

2. A process according to claim 1, wherein said medium contains β-phenylethylamine.

3. A process according to claim 1, wherein said tyramine oxidase has a Km value of $2.7 \times 10^{-5}$M for tyramine.

* * * * *